US011099201B2

(12) United States Patent
Mannhardt

(10) Patent No.: US 11,099,201 B2
(45) Date of Patent: Aug. 24, 2021

(54) DEVICE FOR THE AUTOMATED ANALYSIS OF SOLIDS OR FLUIDS

(71) Applicant: Blue Ocean Nova AG, Eschach (DE)

(72) Inventor: Joachim Mannhardt, Eschach (DE)

(73) Assignee: Blue Ocean Nova AG, Eschach (DE)

(*) Notice: Subject to any disclaimer, the term of this patent is extended or adjusted under 35 U.S.C. 154(b) by 782 days.

(21) Appl. No.: 15/767,977

(22) PCT Filed: Oct. 12, 2016

(86) PCT No.: PCT/EP2016/074502
§ 371 (c)(1),
(2) Date: Apr. 12, 2018

(87) PCT Pub. No.: WO2017/064136
PCT Pub. Date: Apr. 20, 2017

(65) Prior Publication Data
US 2018/0313859 A1 Nov. 1, 2018

(30) Foreign Application Priority Data

Oct. 13, 2015 (DE) ..................... 10 2015 013 140.0

(51) Int. Cl.
G01N 35/02 (2006.01)
G01N 33/02 (2006.01)
(Continued)

(52) U.S. Cl.
CPC .......... G01N 35/025 (2013.01); G01N 33/02 (2013.01); G01N 21/359 (2013.01);
(Continued)

(58) Field of Classification Search
CPC ............ G01N 35/10; G01N 1/00; G01N 1/38; G01N 30/24; G01N 1/2247; G01N 35/02
(Continued)

(56) References Cited

U.S. PATENT DOCUMENTS 3,838,926 A 10/1974 Kato et al.
4,512,953 A * 4/1985 Marsoner ............... G01N 35/10
422/63

(Continued)

FOREIGN PATENT DOCUMENTS

DE 2 221 993 11/1972
DE 689 21 284 T2 6/1995
(Continued)

OTHER PUBLICATIONS

German Office Action for German Application No. 10 2015 013 140.0 dated Jul. 20, 2016 with English translation.

Primary Examiner — Peter J Macchiarolo
Assistant Examiner — Mohammed E Keramet-Amircolai
(74) Attorney, Agent, or Firm — Muncy, Geissler, Olds & Lowe, P.C.

(57) ABSTRACT

The invention relates to a device (1) for the automated analysis of solids or fluids. Said device comprises a first station (5) having a metering unit (51) for the filling of at least one sample chamber (2) with a specified sample quantity, a second station (6) having at least one measurement device (61) for an analysis of the sample situated in a sample chamber (2) and a third station (7) having an emptying device and cleaning device (71, 72) for the at least one sample chamber (2). Moreover, there is provided a transport device (3) for a revolving transport of the at least one sample chamber (2) from one station to the next until the first station (5) is reached again. According to the invention, the measurement device (61) of the second station (6) is a spherical measurement system, through the interior of which it is possible to guide the at least one sample chamber (2).

15 Claims, 1 Drawing Sheet

(51) Int. Cl.
*G01N 21/359* (2014.01)
*G01N 33/00* (2006.01)
*G01N 35/04* (2006.01)

(52) U.S. Cl.
CPC ............ *G01N 2033/0091* (2013.01); *G01N 2035/0441* (2013.01); *G01N 2201/065* (2013.01); *G01N 2201/0632* (2013.01)

(58) Field of Classification Search
USPC ...................................................... 73/864.81
See application file for complete search history.

(56) References Cited

U.S. PATENT DOCUMENTS

| 4,867,559 | A | | 9/1989 | Bach |
| 4,963,743 | A | | 10/1990 | Satake et al. |
| 5,192,505 | A | * | 3/1993 | Sakagami .......... G01N 35/0092 422/63 |
| 5,466,416 | A | * | 11/1995 | Ghaed ................ G01N 21/69 422/52 |
| 5,741,461 | A | * | 4/1998 | Takahashi ........ G01N 35/00594 422/64 |
| 6,553,848 | B1 | * | 4/2003 | Tallentire ............. G01N 1/2247 73/863.41 |
| 6,582,659 | B1 | | 6/2003 | Murata |
| 7,053,373 | B1 | | 5/2006 | Cleary |
| 10,273,703 | B2 | * | 4/2019 | Scatterday ........ F16K 31/52483 |
| 2009/0158863 | A1 | * | 6/2009 | Shanafelter .......... G01N 35/021 73/864.81 |
| 2011/0104007 | A1 | * | 5/2011 | Hirano ................ G01N 35/025 422/63 |
| 2011/0126646 | A1 | * | 6/2011 | Saiki ..................... G01N 21/07 73/864.81 |
| 2013/0333491 | A1 | * | 12/2013 | Seki ....................... G01N 30/16 73/864.81 |
| 2015/0101422 | A1 | * | 4/2015 | Hur ......................... G01N 1/00 73/864.81 |
| 2015/0121996 | A1 | * | 5/2015 | Saari-Nordhaus ..... G01N 30/24 73/61.55 |

FOREIGN PATENT DOCUMENTS

| DE | 698 19 025 T2 | 7/2004 |
| DE | 103 32 800 B3 | 5/2005 |
| DE | 10 2013 006 948 A1 | 10/2014 |
| GB | 1 367 193 | 9/1974 |
| JP | H 05-60765 A | 3/1993 |
| WO | WO 2014/080322 A1 | 5/2014 |
| WO | WO 2015/071706 A1 | 5/2015 |

* cited by examiner

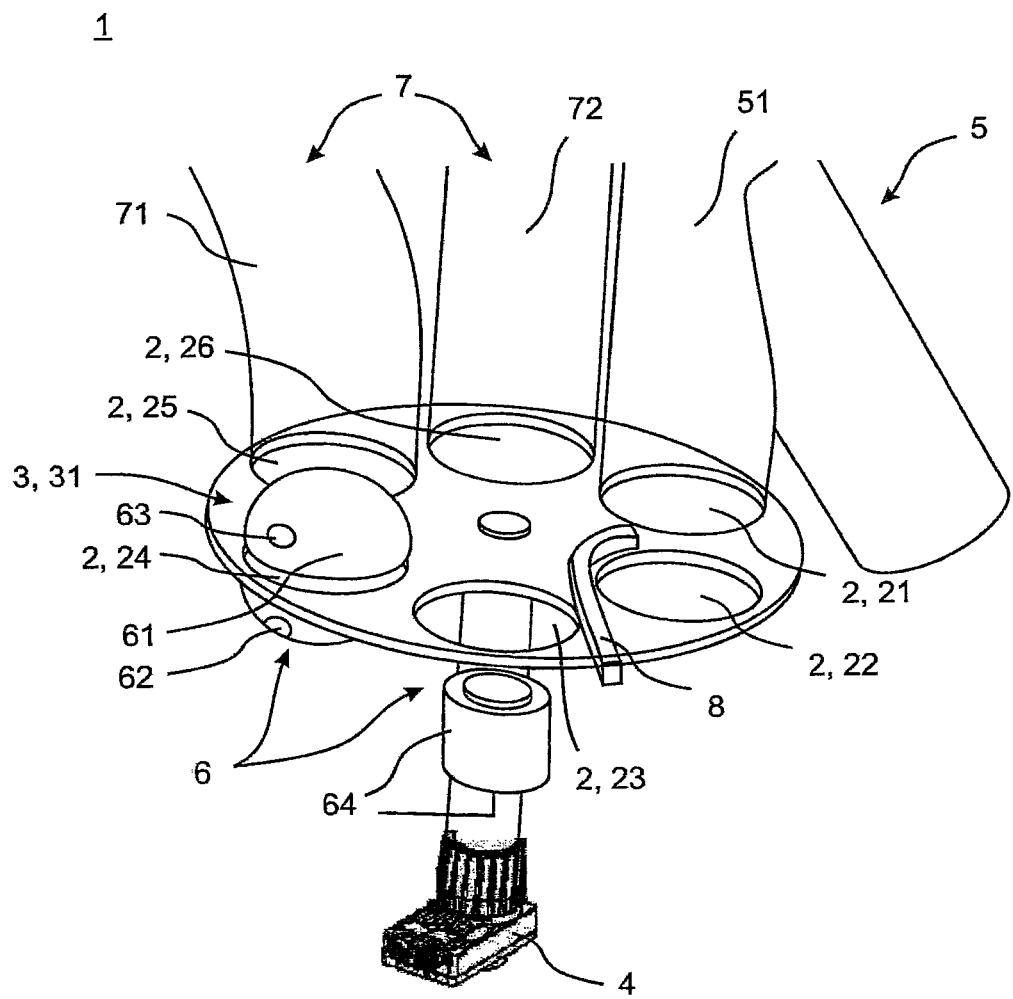

DEVICE FOR THE AUTOMATED ANALYSIS OF SOLIDS OR FLUIDS

This nonprovisional application is a National Stage of International Application No. PCT/EP2016/074502, which was filed on Oct. 12, 2016, and which claims priority to German Patent Application No. 10 2015 013 140.0, which was filed in Germany on Oct. 13, 2015, and which are both herein incorporated by reference.

BACKGROUND OF THE INVENTION

Field of the Invention

The present invention relates to a device for the automated analysis of solids or fluids according to the preamble of claim 1.

Description of the Background Art

In virtually all processing industries, such as, for example, the pharmaceutical industry, the food industry or the chemical industry, the quality control of products is frequently carried out in laboratories away from the actual production process. The main reasons therefor are that the measurement systems for the chemical analysis are highly sensitive and the operation of said systems requires fundamental scientific knowledge. The costs of measurement systems of complex construction do not allow use in production processes at high volumes. In the production environment, there are, in many cases, also hazardous areas, in the vicinity of which it is not possible to use an item of laboratory equipment.

Spectroscopic measurement methods for the quantitative chemical analysis of solids and fluids are already widespread. Optical measurement appliances are known from the publications WO 2014/080322 A1 and WO 2015/071706 A1 for the measurement of the chemical composition or further sample properties of optical thin samples. Especially samples from the agricultural sector are to be analyzable therewith, for example with respect to their proportion of protein or their moisture content.

DE 10 2013 006 948 A1 discloses, as a technical further development, a device for the automated analysis of particles, especially of those which are obtained when machining wood. What is described is a first station having a metering unit for a filling of a separate sample plate with a specified sample quantity, a second station having a measurement device for an analysis of the sample and a third station having an emptying device and cleaning device for a sample plate, as well as a transport device for a revolving transport of the sample plate in a direction from one station to the next until the first station is reached again.

SUMMARY OF THE INVENTION

It is an object of the present invention to further develop a device for the automated analysis of solids or fluids with respect to the degree of automation.

This object is achieved by the device having the features in claim 1. The dependent claims relate to advantageous embodiments and variants of the invention.

The invention includes a device for the automated analysis of solids or fluids. Said device comprises a first station having a metering unit for the filling of at least one sample chamber with a specified sample quantity, a second station having at least one measurement device for an analysis of the sample situated in a sample chamber and a third station having an emptying device and cleaning device for the at least one sample chamber. Moreover, there is provided a transport device for a revolving transport of the at least one sample chamber from one station to the next until the first station is reached again. According to the invention, the measurement device of the second station is a spherical measurement system, through the interior of which it is possible to guide the at least one sample chamber.

The invention consequently provides a device for the automated analysis of particles or fluids, by means of which it is possible to perform analyses in a very rapid and virtually continuously phasic manner, especially a determination of the chemical composition of the samples.

In one revolution, the sample chamber is filled with the sample in the first station, the actual analysis takes place in the second station and an emptying and cleaning takes place in the third station. The cleaned sample chamber is again available for a filling in the first station. The revolving is done in phases, wherein the phase is specified by the longest residence time of the transport device in one of the stations. This period of time generally arises from the duration of the analysis in the second station.

For the filling of the at least one sample chamber, there is provided a metering unit, from which samples are directly introduced in exactly identical quantity into a recess of the transport device. What is important when preparing the measurement sample is not only the provision of the same quantity every time, but also the distribution of the substance in the sample chamber itself. Here, it is envisaged that, firstly, a uniform thickness is set and, secondly, a uniform compression of the substance takes place. For the analysis, especially for the measurement of solid substances, suitably thin measurement samples are prepared in this way in the sample chamber in question. Particularly suitable for thin, layer-type measurement samples are sample chambers which are formed from planar cylindrical recesses in the transport device itself. On the lid side and base side, the sample chambers preferably consist of material transparent for the measurement radiation.

After a filled sample chamber has been fed by the transport device into the second station, the analysis takes place therein. This can be a chemical analysis of a solid, but possibly also an analysis of gaseous or volatile substances. In the case of a gas analysis, it is possible to arrange further measurement devices having gas-conducting connections to the sample chamber. To this end, it is possible to use sealing measures that are customary per se.

The second station having at least one measurement device for an analysis of the sample situated in the sample chamber can be a spherical measurement system having an integrating sphere in the form of a hemisphere with lid element or a photometer sphere consisting of two hemispheres. The lid element can, for example, be planar and have holes or other guide-through means for optical fibers. Said holes serve as passage points for the coupling of light radiation into the interior of the measurement device.

A spherical measurement system can be formed as a spherical light collector composed of quartz or sapphire glass and be completely mirrored, apart from certain passage points for light radiation, in order to achieve a light-collection effect. Equally, aspherical forms are also conceivable. The light beam emerging from the ends of the optical fibers hits the mirrored inner side of the spherical measurement system and is reflected back therefrom to a collection mirror, which couples out light through a nonmirrored window of the photometer sphere. There, it is, for example, possible to arrange a multimode fiber in order to further conduct the light to a detector. It is equally envisaged to couple out the light directly into a spectrometer without further fiber elements. In this way, the photometer sphere is an attachment unit in relation to the detector. With an integrated compact sensor system, process interfaces are set up which can be linked to data management solutions already available on the market. In this way, it is possible to create intelligent process interfaces with integrated fiber-optic spectral sensors which are suitable for direct use in production lines.

The spherical measurement system is, for example, suitable for measurements by means of NIR spectroscopy, in which the sample is illuminated from many sides via the integrating sphere. Here, the integrating sphere mirrored on the inside ensures a homogeneous light distribution on and in the sample. In the measurement system, InGaAs detectors having a high level of sensitivity are, for example, suitable for signal capture. In the case of quantitative determinations, data sets with known content or known concentrations of the substance to be analyzed are created beforehand, as in general in infrared spectroscopy. Equally, it is also possible to consider measurement systems for UV applications.

Like other vibrational spectroscopies, near-infrared spectroscopy is based on the excitation of molecular vibrations by electromagnetic radiation in the near-infrared region. In NIRS, the detection preferably takes place in the near-infrared region within the wavelength range of 760-2500 nm. NIR spectroscopy is, for example, suitable for the determination of the water content in products of many kinds. In particular, quality analyses of agricultural products, such as, for example, cereal, flour and animal feed, can also be investigated in order to determine moistness, protein content and fat content. An online process control in the food industry or in the case of chemical and pharmaceutical products is conceivable too.

In the third station, the sample chamber is emptied, possibly through a suction device into one or more residue containers. The residue containers, too, can be exchangeable for each sample, meaning that the measurement series can be documented reconstructibly in their chronological sequence and be assigned to a batch underlying the measurement sample.

The particular advantage of the invention is that the course of an analysis is fully automated. Usually, there is no longer any need for a manual intervention into the course of the analysis. In particular, the device according to the invention allows an analysis which proceeds at short intervals and is continuously phasic. The sample substances can be directly fed to the metering unit. This means that it is possible to integrate the quality control of the sample material into a production process. In the event of deviations of the measurement values from the predefined nominal values, it is possible, through an appropriate assignment of the sample substance to the batch in question, to intervene in a production process, possibly without delay. The integration of the quality control into production sequences achieves an increase in efficiency and also an associated reduction in production costs.

A further advantage of the invention arises through a distinct compact construction of the measurement device. In particular, it is also possible to realize an advantageous miniaturization of the spherical measurement system without having to design the mechanisms for the coupling-in and coupling-out of light in a constructively more complicated manner. Such fiber-optic measurement components as well as suitable sensor systems and the degree of automation to be achieved therewith contribute very substantially to increasing economical operation.

In an advantageous configuration of the invention, the transport device can comprise a rotary plate in which one sample chamber is integrated or multiple sample chambers are integrated. The rotary plate preferably has as many sample chambers as there are phases in the stations. In this connection, a first measurement sample, for example milk powder, cereal or otherwise pourable or flowable materials, is introduced first of all into a first sample chamber by means of a sample feed. Subsequently, the rotary plate is further rotated by a certain angular dimension and the next phase is initiated. Here, the filled sample chamber enters the integrating sphere, which is preferably secured on the plane of the rotary plate from the side. In the integrating sphere, a transmission measurement, for example, is then carried out. Here, the analysis captures also the interior of a material to be measured, i.e., for example the interior of cereal grains in order to determine the protein content. In the following phase, the sample is removed from the sample chamber, for example by a suction means, and the sample chamber is cleaned, with the result that said chamber is available for the accommodation of a further measurement sample.

In this connection, what is important in the measurement procedure is that a phasic mode of operation of the analysis device is preferably chosen. As a result, the different operational steps are performed during the stoppage of the rotary plate. As a result, an efficient sealing of the individual sample spaces for filling, measuring and cleaning is possible.

Preferably, the rotary plate is designed with an angular division for the sample chambers that is identical in extent and it is arranged in a rotatable manner around a vertical axis. It is thus possible for samples to be successively transferred from a first station, in which the rotary plate is filled, to a second station having a measurement device for an analysis of the sample and to a third station for an emptying and cleaning. With a further phase, the cleaned sample chamber is then transferred again to the first station for a renewed filling. This is followed by a further cycle, in which all the necessary operational steps for the analysis can be carried out simultaneously.

In a particularly preferred configuration, the at least one sample chamber can be integrated on the outer edge of the rotary plate. The rotary plate is rotated by means of a drive motor via a central axis. Sample chambers arranged on the outer edge are at a maximal distance from the drive unit in a region in which there is sufficient installation space for further mechanisms for the filling, measuring and emptying of the sample chambers. On the outer edge of the rotary plate, it is also possible for multiple sample chambers to be designed in a planar manner with an optimal accommodation volume.

Advantageously, a wiper mechanism for achieving a defined sample quantity can be arranged between the first station and the second station. A wiper mechanism removes excess sample material and may possibly also compress the sample. For the wipe-off of excess sample material, it is sufficient to rotate through the rotary plate under an arm immediately guided along the upper side of said rotary plate. In this connection, the arm can reach in a radial direction on the rotary plate over a sample chamber and be held outside, meaning that said arm sweeps across the upper side of the rotary plate and removes the excess sample material with its front edge. For compression, the wiper mechanism can have a blade-type shape. The removal blade is arranged such that it sweeps sample material into the recess of the sample chamber and compresses said sample material while doing so and also removes excess sample material, with the result that, altogether, a reproducible, exact layer thickness is produced.

In a further advantageous configuration of the invention, the second station can consist of multiple measurement mechanisms which are arranged one after the other in the direction of rotation. For the chemical measurement, it is also possible to use multiple measurement methods, for example for the determination of moistness, protein content and fat content of products. Also envisaged are physical measurement mechanisms which necessitate the use of multiple different measurement apparatuses. Further optical measurement mechanisms for checking a correctly filled sample chamber can be positioned upstream, too.

In a further additional embodiment, a further measurement device for the analysis of the sample quantity situated in a sample chamber can be arranged, in the direction of rotation, before the measurement device in the second station. In this phase, the thus prepared sample is examined by means of a detector or a camera as to whether the desired sample thickness has been set and a satisfactory sample processing has occurred.

Advantageously, the at least one sample chamber can be completely formed within the rotary plate. The sample chambers then end with the upper side and lower side of the rotary plate, meaning that there are no protruding projections. This facilitates the through-rotation of the rotary plate through the interior of an integrating sphere. The sample substances can be introduced as a particularly thin layer into planar sample chambers completely integrated in the rotary plate. Here, it is envisaged that, in addition to a uniform thickness of the layer, a uniform compression of the substance also leads to a homogeneous distribution. For the analysis, especially for the measurement of solid substances, suitably thin measurement samples are prepared in this way in the sample chamber in question.

For the measurement of layers of differing thickness, it is possible, in particular, to envisage providing forming interchangeable inserts, by means of which it is possible to realize different depths of sample chambers and thus different layer thicknesses. Said interchangeable inserts can then, as required, be inserted into the sample chambers or, as a substitute for the sample chambers, into the rotary plate. In a particularly simple variant of the invention, the interchangeable inserts are formed as simple plane-parallel plates of differing thickness which are self-evidently transparent for the radiation used for the measurement. Through simple insertion of said plates, it is possible to reduce the depth of the sample chambers and thus the layer thickness. Typical layer thicknesses are within the range of up to 5 mm.

Preferably, the lower side of the base and/or the upper side of a lid of the sample chamber can align with the lower side of the rotary plate and the upper side of the rotary plate, respectively.

In an advantageous configuration of the invention, the at least one sample chamber can be closable in a gas-tight manner in the first station and/or second station and/or third station. In the case of a chemical analysis of gaseous or readily volatile substances, it is possible to arrange further measurement devices with gas-conducting connections to the sample chamber. In this case, the gas-conducting connection must be connected to the sample chamber such that, upon further rotation of the rotary plate, the connection disengages and docks with the following sample chamber. To this end, it is possible to envisage sealing measures which are customary per se. In the case of combustible gases or vapors in concentrations harmful to health, special precautions should be taken with regard to the level of leak-tightness.

Advantageously, the at least one sample chamber can have a base region and/or lid region that is penetrable for optical radiation. Particular preference is given to optically transparent silicate glasses. Thus, it is possible for a sample chamber to be optionally covered with a lid element after the filling and before the transport to the second station.

Advantageously, the transport device can be arranged in a housing under specifiable environmental conditions. Within the housing, it is, for example, possible to set a constant temperature and/or an exactly specified air humidity. Furthermore, such a housing will prevent an uncontrolled escape of gases possibly harmful to health into the environment. Equally, it is possible, by means of inert gases, to prevent a contamination of or change to the measurement sample in an effective manner.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawing which is given by way of illustration only, and thus, is not limitive of the present invention, and wherein the sole FIGURE illustrates an example embodiment, showing a cross-sectional view of an adjustment fitting with sealing of the eccentric receiving space.

FIG. 1 shows schematically one view of a device according to the invention for the automated analysis of solids or fluids.

DETAILED DESCRIPTION

FIG. 1 shows schematically one view of a device 1 for the automated analysis of solids or fluids. Said device contains a first station 5 having a metering unit 51 for the successively phasic filling of, in this case, six sample chambers 2 with a specified sample quantity. A second station 6 contains a spherical measurement system 61 for an analysis of the sample situated in a sample chamber 2 and also a camera as further upstream measurement device 64. A third station 7 is an emptying device 71 and a cleaning device 72 for the sample chambers 2 in question. Moreover, a transport device 3 is implemented as a rotary plate 31 for a revolving transport of the sample chambers 2 from one station to the next. After a complete rotation, the first station 5 is reached again for the filling of the cleaned sample chambers 2. According to the invention, the measurement device 61 of the second station 6 is an integrating sphere, through the interior of which it is possible to guide each of the sample chambers 2.

In FIG. 1, a wiper mechanism 8 is mounted between the first station 5 and the second station 6. Said wiper mechanism 8 comprises an arm guided along the upper side of the rotary plate 31, which arm removes excess sample material projecting above the planar sample chamber 2. For the sake of simplicity, the further mounts of the arm beyond the rotary plate 31 are not depicted.

The six sample chambers 2 are arranged in the rotary plate 31 on the periphery at an angular distance of, in each case, 60°. By means of a drive motor 4, the rotary plate 31 can be further rotated in steps around a vertical axis. In this preferred embodiment, there is positioned in the rotary plate a first sample chamber 21 at the first station 5 for filling. Introduced here are, for example, milk powder, cereal or otherwise pourable or flowable materials. Optionally, it is possible in this position for the measurement sample to be compressed by a stamp guided from above, not depicted in FIG. 1. The second sample chamber 22 is situated, in the direction of rotation, immediately before the arm of the wiper mechanism 8. The third sample chamber 23 is situated in the second station 6 and is examined for a sufficiently good sample quality by means of a camera as further measurement device 64.

Likewise at the second station 6, the fourth sample chamber 24 is situated within the integrating sphere as measurement device 61 for a chemical analysis of the sample. In the integrating sphere, there then takes place, for example, a transmission measurement. In this connection, the integrating sphere 61 consists of a photometer sphere constructed from two half-shells, into the equatorial plane of which the sample chamber in question is introduced phasically. Situated on the lower half-shell of the integrating sphere 61 is an entrance window 62 for the measurement radiation. The upper half-shell of the integrating sphere 61 has an exit window 63, through which the measurement radiation can reach a detector unit. Detector unit, and the further optical imaging units and filters situated outside the integrating sphere 61, are not depicted in FIG. 1 for the sake of simplicity. These additional mechanisms are known in principle and can, for example, be gathered from the above-cited prior art by a person skilled in the art.

The fifth sample chamber 25 is below a suction pipe of the emptying device 71 of the third station 7, via which pipe the sample material is largely removed apart from negligible residues. The sixth sample chamber 26 is situated in the third station 7 at the site of the cleaning device 72, in which the sixth sample chamber 26 is completely cleaned, so that it can be further rotated into the first station 5 for filling. Altogether, the rotary plate consequently has exactly as many sample chambers as there are mechanisms altogether in the stations in the measurement cycle for the preparation and measurement for one run.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for the automated analysis of solids or fluids, comprising:
    a first station having a metering unit that performs a filling of at least one sample chamber with a specified sample quantity to form a sample in the at least one sample chamber;
    a second station having at least one measurement device for an analysis of the sample situated in the at least one sample chamber;
    a third station having an emptying device and a cleaning device for the at least one sample chamber; and
    a transport device for a revolving transport of the at least one sample chamber from one station to the next until the first station is reached again,
    wherein the measurement device of the second station is a spherical light collector,
    wherein an interior of the measurement device is adapted to receive the at least one sample chamber such that the sample passes radially through the spherical light collector.

2. The device as claimed in claim 1, wherein the transport device comprises a rotary plate in which the at least one sample chamber is integrated or multiple sample chambers of the at least one sample chamber are integrated.

3. The device as claimed in claim 2, wherein the at least one sample chamber is integrated on the outer edge of the rotary plate in a same plane as the rotary plate.

4. The device as claimed in claim 1, wherein the at least one sample chamber is completely formed within a rotary plate of the transport device such that the at least one sample chamber ends at a first planar surface of the rotary plate and at a second planar surface of the rotary plate, the first planar surface being opposite the second planar surface.

5. The device as claimed in claim 1, wherein a rotary plate of the transport device is adapted to receive interchangeable inserts, the interchangeable inserts having different depths.

6. The device as claimed in claim 1, wherein a lower side of a base of the at least one sample chamber and/or an upper side of a lid of the at least one sample chamber aligns with a lower side of a rotary plate of the transport device and an upper side of the rotary plate, respectively.

7. The device as claimed in claim 1, further comprising: a wiper mechanism that removes excess sample material to achieve a defined sample quantity for the sample is arranged between the first station and the second station.

8. The device as claimed in claim 1, wherein the second station comprises multiple measurement mechanisms which are arranged one after the other at different rotation positions in the direction of rotation.

9. The device as claimed in claim 1, further comprising:
    a further measurement device for the analysis of the sample quantity situated in a sample chamber is arranged, in the direction of rotation, before the measurement device in the second station.

10. The device as claimed in claim 1, wherein the at least one sample chamber is closable in a gas-tight manner in the first station and/or second station and/or third station.

11. The device as claimed in claim 1, wherein the at least one sample chamber has a base region and/or a lid region that is penetrable by optical radiation.

12. The device as claimed in claim 1, wherein the transport device is arranged in a housing under specifiable environmental conditions.

13. The device as claimed in claim 1, wherein the spherical light collector includes a first hemispherical light collector disposed on a first side of a rotary plate of the transport device and a second hemispherical light collector disposed on a second side of the rotary plate of the transport device, wherein the rotary plate carries the sample between the first hemispherical light collector and the second hemispherical light collector along the equatorial plane, the first hemispherical light collector being opposite the second hemispherical light collector.

14. The device as claimed in claim 1, wherein the transport device includes a rotary plate and a drive to rotate the rotary plate, the at least one sample chamber being at least three sample chambers, wherein the rotary plate is a circular plate that includes at least three throughholes for receiving interchangeable inserts corresponding to the at least three sample chambers, and wherein the first station, the second station, and the third station each correspond to one of the at least three throughholes.

15. The device as claimed in claim 1, wherein the measurement device performs a chemical analysis of the sample via a measurement radiation transmitted into the spherical light collector and subsequently detected from the spherical light collector.

\* \* \* \* \*